(12) United States Patent
Murphy et al.

(10) Patent No.: US 11,630,057 B2
(45) Date of Patent: *Apr. 18, 2023

(54) DEFORMULATION TECHNIQUES FOR DEDUCING THE COMPOSITION OF A MATERIAL FROM A SPECTROGRAM

(71) Applicant: X Development LLC, Mountain View, CA (US)

(72) Inventors: Gearoid Murphy, Mountain View, CA (US); Artem Goncharuk, Mountain View, CA (US); Lance Co Ting Keh, La Crescenta, CA (US); Diosdado Rey Banatao, Los Altos Hills, CA (US); Sujit Sanjeev, Mountain View, CA (US)

(73) Assignee: X Development LLC, Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/658,765

(22) Filed: Apr. 11, 2022

(65) Prior Publication Data

US 2022/0236171 A1    Jul. 28, 2022

Related U.S. Application Data

(63) Continuation of application No. 16/948,760, filed on Sep. 30, 2020, now Pat. No. 11,353,394.

(51) Int. Cl.
*G01N 21/31*   (2006.01)
*G16C 20/20*   (2019.01)
(Continued)

(52) U.S. Cl.
CPC .............. *G01N 21/314* (2013.01); *G01J 3/28* (2013.01); *G16C 20/20* (2019.02); *G01N 33/52* (2013.01); *G01N 2021/3155* (2013.01)

(58) Field of Classification Search
CPC ................. G01N 21/314; G01N 33/52; G01N 2021/3155; G01J 3/28; G16C 20/20; G16C 20/70; Y02W 30/62; G06N 20/00
See application file for complete search history.

(56) References Cited

U.S. PATENT DOCUMENTS

| | | | |
|---|---|---|---|
| 6,675,106 B1 * | 1/2004 | Keenan ................. | G06F 17/141 702/194 |
| 8,452,716 B2 * | 5/2013 | Howley ................. | G01N 21/65 706/12 |

(Continued)

FOREIGN PATENT DOCUMENTS

WO    2019195737    10/2019

OTHER PUBLICATIONS

"Cholesky Decomposition", Wikipedia, Available Online at: https://en.wikipedia.org/wiki/Cholesky_decomposition, Accessed from Internet on Jan. 22, 2021, pp. 1-11.

(Continued)

*Primary Examiner* — David P Porta
*Assistant Examiner* — Gisselle M Gutierrez
(74) *Attorney, Agent, or Firm* — Kilpatrick Townsend & Stockton LLP (57) ABSTRACT

The present disclosure relates to techniques for deformulating the spectra of arbitrary compound formulations such as polymer formulations into their chemical components. Particularly, aspects of the present disclosure are directed to obtaining an initial set of spectra for a plurality of samples comprising pure samples and composite samples, constructing a basis set of spectra for a plurality of pure samples based on the initial set of spectra, and providing or outputting the basis set of spectrum. The basis set of spectra is constructed in an iterative process that attempts to decompose, using a decomposition algorithm or model, the spectrum from the initial set of spectra in order to differentiate the pure samples (Continued)

from the composite samples. The basis set of spectra may then be used to deduce the composition of a material from a spectrogram.

20 Claims, 6 Drawing Sheets

(51) Int. Cl.
*G01J 3/28* (2006.01)
*G01N 33/52* (2006.01)

(56) References Cited

U.S. PATENT DOCUMENTS

| | | | |
|---|---|---|---|
| 10,023,323 | B1 | 7/2018 | Roberts et al. |
| 10,710,119 | B2 * | 7/2020 | Kumar ............... G06N 3/08 |
| 11,353,394 | B2 | 6/2022 | Murphy et al. |
| 2004/0111220 | A1 * | 6/2004 | Ochs ............... G06K 9/624 702/19 |
| 2007/0272775 | A1 | 11/2007 | Szilvassy et al. |
| 2021/0020276 | A1 * | 1/2021 | Da Costa Martins ............... G06K 9/6247 |
| 2021/0372909 | A1 | 12/2021 | Højlund-Nielsen et al. |

OTHER PUBLICATIONS

"KnowItAll Academic Edition—Free Chemistry Software", Wiley Science Solutions, Available Online at: https://sciencesolutions.wiley.com/academic-edition/, Accessed from Internet on Jan. 22, 2021, pp. 1-2.
U.S. Appl. No. 16/948,760, "Corrected Notice of Allowability", dated Feb. 22, 2022, 2 pages.
U.S. Appl. No. 16/948,760, Notice of Allowance, dated Feb. 3, 2022, 10 pages.
International Application No. PCT/US2021/044783, International Search Report and Written Opinion, dated Nov. 19, 2021, 13 pages.
Rani et al., "Miniaturized Near-Infrared (MicroNIR) Spectrometer in Plastic Waste Sorting", Materials, vol. 12, Issue 17, Aug. 2019, pp. 1-13.
Scott et al., "Identification of Plastic Waste Using Spectroscopy and Neural Networks", Polymer Engineering and Science, vol. 35, No. 12, Jun. 1995, pp. 1011-1015.
Vazquez-Guardado et al., "Multi-Spectral Infrared Spectroscopy for Robust Plastic Identification", Applied Optics, vol. 54, No. 24, Aug. 20, 2015, pp. 7396-7405.
Zhu et al., "Plastic Solid Waste Identification System Based on Near Infrared Spectroscopy in Combination with Support Vector Machine", Advanced Industrial and Engineering Polymer Research, vol. 2, 2019, pp. 77-81.

* cited by examiner

DEFORMULATION TECHNIQUES FOR DEDUCING THE COMPOSITION OF A MATERIAL FROM A SPECTROGRAM

CROSS-REFERENCE TO RELATED APPLICATIONS

This application is a continuation of U.S. patent application Ser. No. 16/948,760, filed Sep. 30, 2020, the entirety of which is incorporated herein by reference.

FIELD

The present disclosure relates to deformulation of spectra for arbitrary compound formulations, and in particular to techniques for deformulating the spectra of arbitrary compound formulations such as polymer formulations into their chemical components.

BACKGROUND

Plastic products are predominantly single-use and frequently not recycled. Annual production of plastic worldwide is approximately 350 million tons, of which approximately 10% ends up being recycled, 12% is incinerated, and the remainder (78%) accumulates in landfills or the natural environment, where it takes nearly 500-1,000 years to degrade. Plastic production is expected to double by 2030 and triple by 2050. Recycling processes depend on accurate material characterization, sorting, and decomposition yield prediction.

Vibrational spectroscopy is one approach to characterize the interaction of matter with light, and affords a technique for identifying a material by a unique pattern of spectral features. Covalent bonds between component atoms in a molecule absorb infrared (IR) radiation at characteristic frequencies. The different vibrations of the different functional groups in the molecule give rise to spectral features, such as peaks and bands, of differing intensity. Another factor that determines the feature intensity in infrared spectra is the concentration of molecules in the sample. As a result, many materials exhibit a characteristic absorbance pattern in the infrared spectrum, which can be measured by spectroscopy and can be used to identify the material. Identification of materials by IR spectroscopy forms the foundation of many analytical techniques in materials processing, such as material sorting. For example, an unidentified material is characterized by IR radiation to generate a characteristic absorbance spectrum, which is then compared to a library of characteristic absorbance spectra for known materials to find a match. The match involves evaluating a fit across multiple features in terms of both energy and intensity. In some cases, as when intensity-calibrated instruments are used, the composition of the unidentified material can also be determined from IR spectroscopy. Unfortunately, chemical spectral databases typically contain data for pure substances or precisely quantified mixtures of industrial or scientific importance. Contaminated materials and complex blends are less frequently included. When characteristic spectra are unavailable, prediction of chemical composition of non-standard materials, such as waste materials, becomes much more difficult.

SUMMARY

Techniques are provided (e.g., a method, a system, non-transitory computer-readable medium storing code or instructions executable by one or more processors) for deformulating the spectra of arbitrary compound formulations such as polymer formulations into their chemical components, using machine learning (ML) models implemented in deep learning networks.

In various embodiments, a computer-implemented method is provided comprising: obtaining an initial set of spectra for a plurality of samples comprising pure samples and composite samples; constructing a basis set of spectra for a plurality of pure samples based on the initial set of spectra, wherein the constructing the basis set of spectra comprises: (i) selecting a spectrum from the initial set of spectra; (ii) attempting to decompose, using a decomposition algorithm or model, the selected spectrum based on spectrum within the basis set of spectra, (iii) when the selected spectrum is unable to be decomposed, adding the selected spectrum to the basis set of spectra; and (iv) in response to adding the selected spectrum to the basis set of spectra, performing an exclusion search of the basis set of spectra that includes iteratively removing each spectrum from the basis set of spectra, attempting to decompose, using the decomposition algorithm or model, each removed spectrum based on spectrum remaining within the basis set of spectra, and when a removed spectrum is able to be decomposed, identifying the removed spectrum as a composite sample and leaving the removed spectrum out of the basis set of spectra, or when the removed spectrum is unable to be decomposed, identifying the removed spectrum as a pure sample and adding the spectrum back into the basis set of spectra, wherein steps (i)-(v) are performed iteratively until all spectrum from the initial set of spectra are processed; and providing the basis set of spectrum.

In some embodiments, the computer-implemented method further comprises prior to constructing the basis set, sorting the initial set of spectra based on a number of peaks observed within each spectrum, wherein the spectrum are selected from the initial set of spectra starting at spectrum with a least amount of peaks and proceeding through the initial set of spectra to spectrum with a greatest amount of peaks.

In some embodiments, the decomposition algorithm or model is a decomposition algorithm and the decomposition algorithm is the Cholesky algorithm, the Cholesky-Banachiewicz algorithm, the Cholesky-Crout algorithm, or any combination thereof.

In some embodiments, the decomposition algorithm or model is a decomposition model and the decomposition model is implemented in an artificial neural network.

In some embodiments, the decomposition model is a linear regression or spectral clustering model and the linear regression or spectral clustering model is learned based on the Cholesky algorithm, the Cholesky-Banachiewicz algorithm, the Cholesky-Crout algorithm, or any combination thereof.

In some embodiments, the attempting to decompose the selected spectrum or the removed spectrum comprises determining whether the selected spectrum or the removed spectrum is reproducible based on the spectrum within the basis set of spectra, and wherein the determining whether the selected spectrum or the removed spectrum is reproducible is a flexible determination made in accordance with a predetermined threshold set at greater than or equal to 65% reproducibility.

In some embodiments, the computer-implemented method further comprises: obtaining a spectrogram for a material; inputting the spectrogram into a neural network model trained for classification of chemical components using a loss function and the basis set of spectra; identifying and classifying, using the neural network model, one or more chemical components within the spectrogram; and outputting, using the neural network, the classification for each of the one or more chemical components.

In some embodiments, the neural network model comprises a plurality of model parameters identified using a set of training data comprising the basis set of spectra maps, and wherein the plurality of model parameters are identified using the set of training data based on minimizing the loss function.

In some embodiments, the computer-implemented method further comprises using the classification for each of the one or more chemical components to characterize the material, sort the material from other materials, predict decomposition yield of the material, or any combination thereof.

In some embodiments, the computer-implemented method further comprises chemically and/or physically decomposing the material into the one or more chemical components, and manufacturing a target product using the one or more chemical components based on the characterization, sorting and/or yield prediction of the material.

In some embodiments, a system is provided that includes one or more data processors and a non-transitory computer readable storage medium containing instructions which, when executed on the one or more data processors, cause the one or more data processors to perform part or all of one or more methods disclosed herein.

Some embodiments of the present disclosure include a system including one or more data processors. In some embodiments, the system includes a non-transitory computer readable storage medium containing instructions which, when executed on the one or more data processors, cause the one or more data processors to perform part or all of one or more methods and/or part or all of one or more processes disclosed herein.

Some embodiments of the present disclosure include a computer-program product tangibly embodied in a non-transitory machine-readable storage medium, including instructions configured to cause one or more data processors to perform part or all of one or more methods and/or part or all of one or more processes disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the claimed subject matter. Thus, it should be understood that although the present claimed subject matter has been specifically disclosed by embodiments and optional features, modification and variation of the concepts herein disclosed may be resorted to by those skilled in the art, and that such modifications and variations are considered to be within the scope of this disclosure as defined by the appended claims.

BRIEF DESCRIPTION OF THE DRAWINGS

The present disclosure will be better understood in view of the following non-limiting figures, in which.

In the appended figures, similar components and/or features can have the same reference label. Further, various components of the same type can be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION

The ensuing description provides preferred exemplary embodiments only, and is not intended to limit the scope, applicability or configuration of the disclosure. Rather, the ensuing description of the preferred exemplary embodiments will provide those skilled in the art with an enabling description for implementing various embodiments. It is understood that various changes may be made in the function and arrangement of elements without departing from the spirit and scope as set forth in the appended claims.

Specific details are given in the following description to provide a thorough understanding of the embodiments. However, it will be understood that the embodiments may be practiced without these specific details. For example, circuits, systems, networks, processes, and other components may be shown as components in block diagram form in order not to obscure the embodiments in unnecessary detail. In other instances, well-known circuits, processes, algorithms, structures, and techniques may be shown without unnecessary detail in order to avoid obscuring the embodiments.

Also, it is noted that individual embodiments may be described as a process which is depicted as a flowchart, a flow diagram, a data flow diagram, a structure diagram, or a block diagram. Although a flowchart or diagram may describe the operations as a sequential process, many of the operations may be performed in parallel or concurrently. In addition, the order of the operations may be re-arranged. A process is terminated when its operations are completed, but could have additional steps not included in a figure. A process may correspond to a method, a function, a procedure, a subroutine, a subprogram, etc. When a process corresponds to a function, its termination may correspond to a return of the function to the calling function or the main function.

I. INTRODUCTION

Mechanical recycling, which describes physical processing to reuse or reform waste materials, is limited in its applicability to mixed, composite, and contaminated waste streams. For example, mechanical recycling typically employs mechanical separation and reformation processes that are insensitive to chemical contaminants and may be unable to modify the chemical structure of waste material. Chemical recycling may resolve the limitations of mechanical recycling by breaking the chemical bonds of waste materials into smaller molecules. For example, in the case of polymeric materials, chemical recycling may provide an avenue to recover oligomers, monomers, or even basic molecules from a plastic waste feedstock. In the case of polymers, chemical recycling processes may include operations to depolymerize and dissociate the chemical makeup of a complex plastic product, such that by-products can be up-cycled into feedstocks for new materials.

Elements of chemical recycling may permit a material to be repeatedly dissociated into primary feedstock materials. In this way, rather than being limited by chemical structure and material integrity to a limited number of physical processes, as in mechanical recycling, the products of chemical recycling may include basic monomers (ethylene, acrylic acid, lactic acid, vinyl, etc.), feedstock gases (carbon monoxide, methane, ethane, etc.), or elemental materials (sulfur, carbon, etc.). As such, chemical recycling may permit improved implementation of reuse and recycling strategies based on chemical conversion of a waste material.

Successful implementation of chemical recycling may rely at least in part on accurate identification of waste feedstocks by spectroscopic characterization. For example, a preliminary analysis may be performed to answer fundamental questions about the nature of the unknown material. Spectroscopic methods, such as infrared spectroscopy or x-ray fluorescence spectroscopy might be used for the preliminary analysis to characterize or identify a material by a characteristic pattern of spectral features. The results of the characterization or identification of the material from the preliminary analysis may then be used to inform subsequent choices in later stages of analysis. Chemical spectral libraries or databases used in the preliminary analysis typically contain data for pure substances or precisely quantified mixtures. However, typically there is a lack of accurate descriptive labelling on the spectral libraries or databases. For example, there are many library or database instances of polyethylene variants but there is very little by way of descriptive labelling to capture the precise nature of the polymer branching, the presence of additives and other relevant information such as crystallinity and tacticity. While generalized characteristic spectra may suffice to characterize or identify the core components of a high-purity waste material, the presence of contaminants or additives may interfere with spectroscopic characterization. Furthermore, some less commonly used materials, contaminated materials, and blends are less frequently included in spectral libraries or databases much less provided with accurate descriptive labeling. When characteristic spectra with accurate descriptive labeling are unavailable, prediction of chemical composition of non-standard materials, such as waste materials, becomes much more difficult. Thus, conventional techniques for deformulating the spectra of arbitrary compound formulations into their chemical components still requires expert users in order to guide algorithms and software when determining how to associate specific marker peaks with possible substances for determining the molecular composition.

To address the aforementioned limitations and others, the deformulation techniques disclosed herein construct a basis set of spectra for a plurality of pure samples based on an initial set of spectra for a plurality of samples comprising pure samples and composite samples. The basis set of spectra is constructed in an iterative process that attempts to decompose, using a decomposition algorithm or model, the spectrum from the initial set of spectra in order to differentiate the pure samples from the composite samples. The basis set of spectra may then be used to deduce the composition of a material from a spectrogram.

As used herein, "pure" samples refers to any chemical component or compound that cannot be further decomposed into smaller chemical components in accordance with the Beer-Lambert assumption. For example, a mixture of poly (propenoate) (acrylic), aramid, and polyamide can be decomposed into its individual components [poly(propenoate) (acrylic)]+[aramid]+[polyamide] in accordance with the Beer-Lambert assumption; however, each of these individual components would be consider as "pure" because they cannot be further decomposed in accordance with the Beer-Lambert assumption. As used herein, "composite" samples refers to mixtures of chemical components or compounds that are physically combined. While example embodiments described herein center on polymeric samples and materials or organic chemical samples and materials, these are meant as non-limiting, illustrative embodiments. Embodiments of the present disclosure are not limited to such materials, but rather are intended to address material processing operations for which a wide array of materials serve as potential feedstocks for a material recycling and/or up-cycling process. Such materials may include, but are not limited to, metals, glass, bio-polymers such as ligno-cellulosic materials, visco-elastic materials, minerals such as rare earth containing materials, as well as complex composite materials or devices.

One illustrative embodiment of the present disclosure is directed to a computer implement method that includes: obtaining an initial set of spectra for a plurality of samples comprising pure samples and composite samples; constructing a basis set of spectra for a plurality of pure samples based on the initial set of spectra, wherein the constructing the basis set of spectra comprises: (i) selecting a spectrum from the initial set of spectra; (ii) attempting to decompose, using a decomposition algorithm or model, the selected spectrum based on spectrum within the basis set of spectra, (iii) when the selected spectrum is unable to be decomposed, adding the selected spectrum to the basis set of spectra; and (iv) in response to adding the selected spectrum to the basis set of spectra, performing an exclusion search of the basis set of spectra that includes iteratively removing each spectrum from the basis set of spectra, attempting to decompose, using the decomposition algorithm or model, each removed spectrum based on spectrum remaining within the basis set of spectra, and when a removed spectrum is able to be decomposed, identifying the removed spectrum as a composite sample and leaving the removed spectrum out of the basis set of spectra, or when the removed spectrum is unable to be decomposed, identifying the removed spectrum as a pure sample and adding the spectrum back into the basis set of spectra, where steps (i)-(v) are performed iteratively until all spectrum from the initial set of spectra are processed; and providing or outputting the basis set of spectrum.

As used herein, the terms "substantially," "approximately" and "about" are defined as being largely but not necessarily wholly what is specified (and include wholly what is specified) as understood by one of ordinary skill in the art. In any disclosed embodiment, the term "substantially," "approximately," or "about" may be substituted with "within [a percentage] of" what is specified, where the percentage includes 0.1, 1, 5, and 10 percent. As used herein, when an action is "based on" something, this means the action is based at least in part on at least a part of the something.

Advantageously, these approaches build a basis set of spectra (i.e., a library or database of spectra) with fine grained labeling due to the characteristic nature of the spectra representing only "pure" samples. For example, all or substantially all additives and misleading information associated with the additives has been removed from the spectra (as compared to conventional libraries or databases of spectra such as the initial set of spectra) such that characteristics of the spectra are directly relatable to the "pure" samples and can be used to more accurately train models to deduce the composition of a material.

II. TECHNIQUES FOR DECOMPOSING INPUT SPECTRA INTO CHEMICAL COMPONENTS

Figure 1:
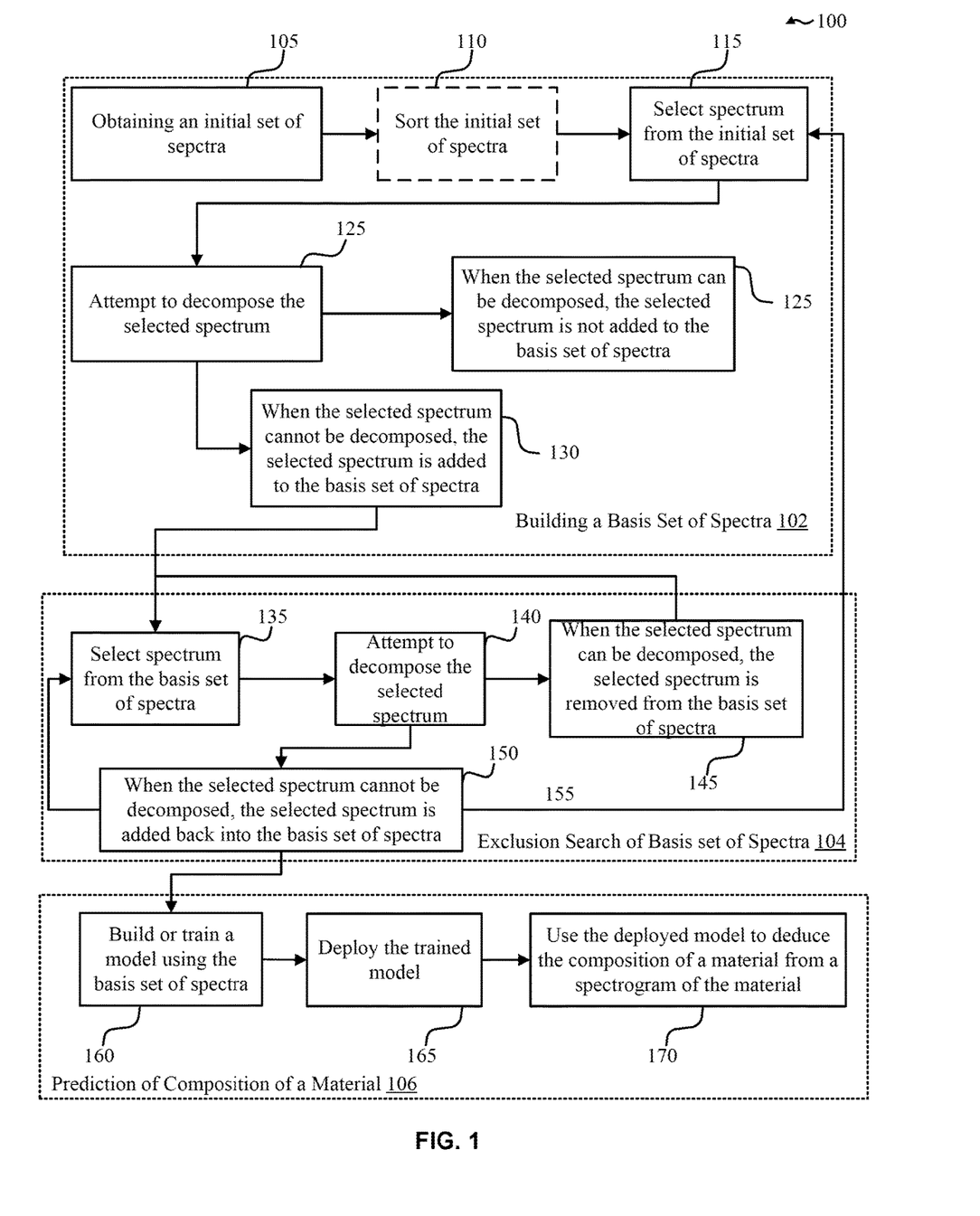
FIG. 1 illustrates an example workflow for decomposing input spectra into their respective chemical components and building a basis set of spectra representing pure samples that can be used to ultimately deduce the composition of a material from a spectrogram, in accordance with some embodiments of the present disclosure.
Figure 3:
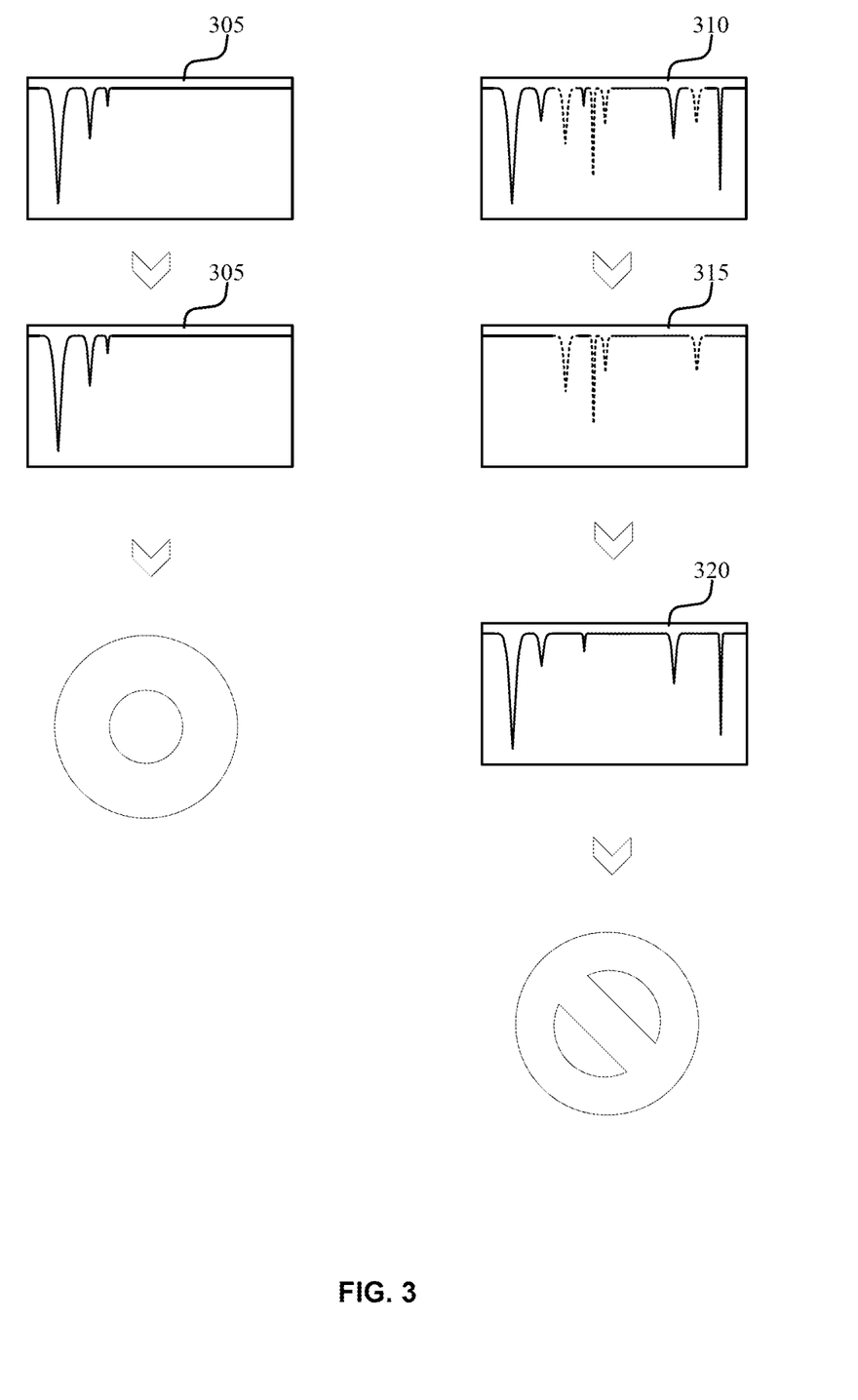
FIG. 3 illustrates an exemplary decomposition process in accordance with some embodiments of the present disclosure.
Figure 4:
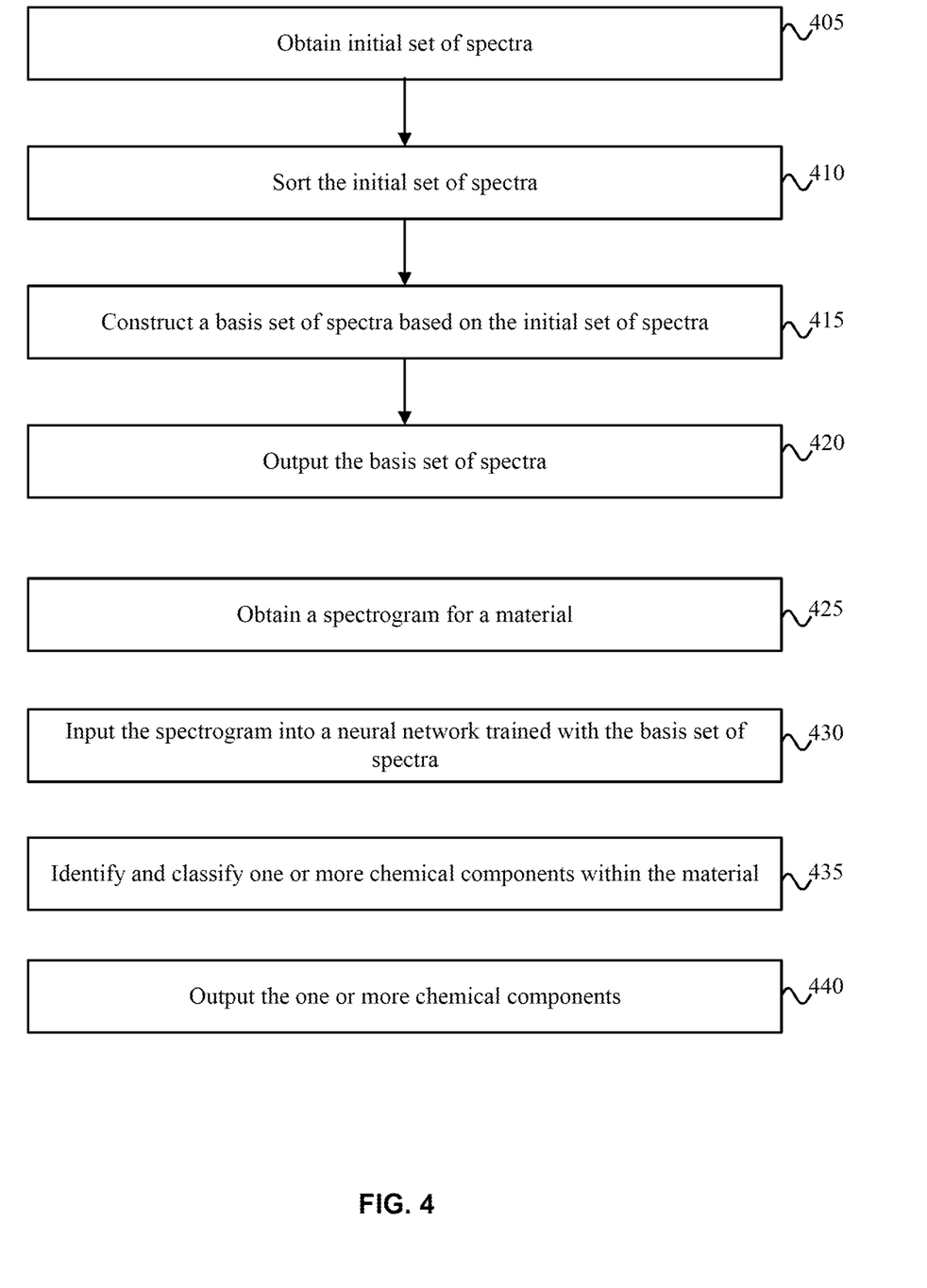
FIG. 4 illustrates an example flow describing a method for deducing the composition of the material from a spectrogram using a neural network model trained on a basis set of spectra representing pure samples obtained in accordance with some embodiments of the present disclosure.

FIGS. 1, 3 and 4 depict simplified block diagrams or flowcharts depicting processing performed for automatically decomposing input spectra into their respective chemical components for building a basis set of spectra representing pure samples according to various embodiments. The steps of FIGS. 1, 3, and 4 may be implemented in the system environment of FIG. 5, for example. As noted herein, the flowcharts of FIGS. 1, 3, and 4 illustrate the architecture, functionality, and operation of possible implementations of systems, methods, and computer program products according to various embodiments of the present disclosure. In this regard, each block in the flowchart or block diagrams may represent a module, segment, or portion of code, which comprises one or more executable instructions for implementing the specified logical functions. It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combination of blocks in the block diagrams and/or flowchart illustration, can be implemented by special purpose hardware-based systems that perform the specified functions or acts, or combinations of special purpose hardware and computer instructions.

FIG. 1 illustrates an example workflow 100 for decomposing input spectra into their respective chemical components and building a basis set of spectra representing pure samples that can be used to ultimately deduce the composition of a material from a spectrogram, in accordance with some embodiments of the present disclosure. As shown in FIG. 1, the workflow 100 is subdivided into sub-processes including building of the basis set of spectra 102, an exclusion search of the basis set of spectra 104, and prediction of a composition of a material 106. The building of the basis set 102 includes various steps to acquire an initial set of spectra for a plurality of compounds and building the basis set from the initial set of spectra. As part of the building of the basis set 102, at step 105, an initial set of spectra is obtained comprising spectra for a plurality of samples comprising pure samples and composite samples. The initial set of spectra comprises more than 50, more than 100, or more than 500 separate spectrum for pure samples and composite samples. In some embodiments, the initial set of spectra are obtained by a computing device from one or more private or public library or database sources, such as NIST WebBook, ChemSpider, Spectra Data Base System (SDBS), NMRShiftDB or the like. The private or public database sources may be a centralized, standards compliant, data repository for chemical structure data, including chemical identifiers or identification numbers, such as CAS numbers, chemical structures according to various structural representation formats, and supporting spectral evidence. Spectral evidence may include standard, uncalibrated, or intensity-calibrated spectra, for example vibrational spectra such as FTIR-ATR spectra, collected from pure samples and/or composite samples.

Figure 2:
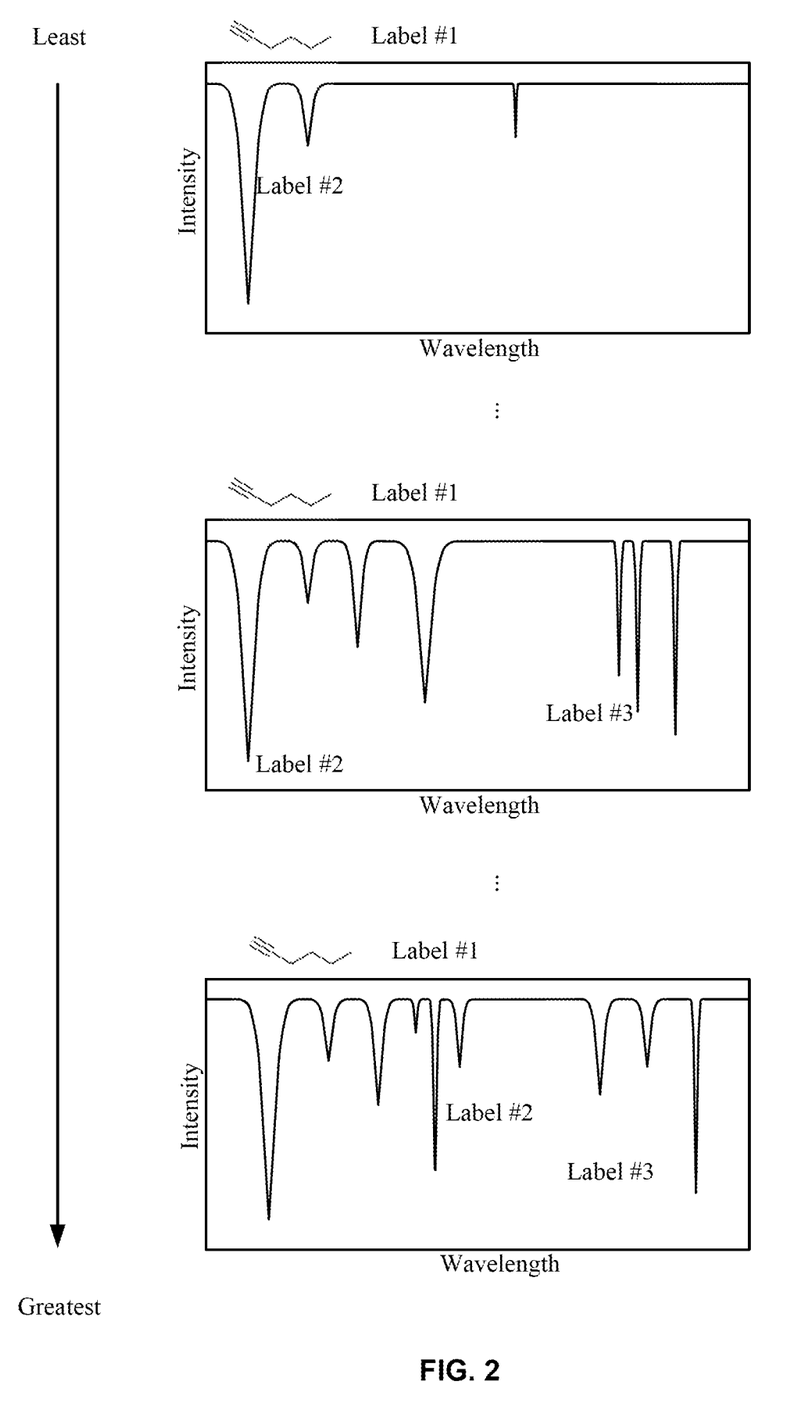
FIG. 2 illustrates example spectra and an exemplary sorting process in accordance with some embodiments of the present disclosure.

The initial set of spectra includes individual spectrum for each pure sample and/or composite sample obtained from one or more libraries or databases. As illustrated in FIG. 2, a spectrum can describe an emission spectrum or an absorbance spectrum. An emission spectrum can show radiation intensity as a function of wavelength, as generated by measuring radiation output by a radiation source. By contrast, an absorbance spectrum describes an intensity of absorption of radiation by a material as a function of energy, which can be expressed as frequency, wavelength, wavenumber, or energy, and can correspond to radiation reflected or transmitted by the material. In the context of chemical spectral libraries or databases described herein, absorbance spectra can describe the characteristic pattern of spectral features for non-emissive materials. As should be understood, the initial set of spectra may not have accurate labeling. For example, there may be coarse descriptive labelling within the spectral evidences that fails to capture the precise nature of pure-control samples or standard composites such as the polymer branching, the presence of additives and other relevant information such as crystallinity and tacticity.

At optional step 110, the initial set of spectra may be sorted based on one or more characteristics of the spectra. For example, the initial set of spectra may be sorted based on the number of peaks within each spectrum. In this instance, it is assumed that spectrum with smaller amounts of peaks will likely be associated with pure samples; whereas spectrum with a larger number of peaks will likely be associated with non-pure samples and likely include composites samples. As illustrated in FIG. 2, the spectra may be sorted based on the number of peaks within each spectrum from spectrum having a least amount of peaks to spectrum having the greatest number of peaks.

At step 115, a spectrum from the initial set of spectra is selected to serve as an input to a decomposition algorithm or model. The decomposition algorithm or model, as described in more detail with reference to FIG. 3, may form a part of the techniques described herein to decompose input spectra into their respective chemical components. The spectrum may be selected from the initial set of spectra by various approaches. For example, the initial set of spectra may be pre-processed to filter materials of limited significance for a materials processing facilities, such as proteins and other biological molecules, and the spectrum may be selected from the filtered spectra. As another example, the spectrum may be selected to exclude data for complex materials, such as co-polymers or polycyclic aromatic hydrocarbons. As another example, the spectrum may be selected in accordance with the sorting performed in optional step 110 (e.g., the spectrum may be selected from the initial set of spectra starting at spectrum with a least amount of peaks and proceeding through the initial set of spectra to spectrum with a greatest amount of peaks).

At step 120, the decomposition algorithm or model attempts to reproduce the selected spectrum based on spectrum within the basis set of spectra. According to the Beer-Lambert assumption, linear combinations of chemical components in a mixture should be represented as linear combinations of their respective spectra within a spectrum representative of the mixture. As such, any pure sample represented by a selected spectrum should not be able to be decomposed into individual components because it is not a linear combination of chemical components (it is in fact a single chemical component). Consequently, any selected spectrum representative of a pure sample should not be reproducible using a linear combination of spectra. In contrast, any composite sample represented by a selected spectrum should be able to be decomposed into its individual chemical components because it is a linear combination of chemical components (it is in fact multiple chemical components). Consequently, any selected spectrum representative of a composite sample should be reproducible using a linear combination of spectra for the individual chemical components being limited by availability of spectra (i.e., spectra within the basis set) for the individual chemical components.

As illustrated in FIG. 3, the selected spectrum may be spectrum representative of a pure sample 305 or spectrum representative of a composite sample 310. The decomposition algorithm or model should not be able to decompose the selected spectrum representative of a pure sample 305 because it is already in its simplest form. However, the decomposition algorithm or model should be able to decompose the selected spectrum representative of the composite sample 310 into its individual chemical components 315 and 320 because it is not in its simplest form (a linear combination of chemical components). Accordingly, the decomposition algorithm or model works to differentiate spectrum representative of a pure sample, which are intended to be added into the basis set of spectra, from spectrum representative of composite samples, which are not intended to be added to the basis set of spectra.

The decomposition algorithm or model can be any algorithm or model capable of reproducing the selected spectrum based on spectrum within the basis set of spectra. The basis set of spectra may comprise more than 50, more than 100, or more than 500 separate spectrum for pure samples at any one time, e.g., for decomposition of selected spectrum and/or after adding processed selected spectrum to the basis set of spectra. In some instances, the decomposition algorithm is the Cholesky algorithm used to calculate a decomposition matrix related to the selected spectrum. In other instances, the decomposition algorithm is the Cholesky-Banachiewicz algorithm or the Cholesky-Crout algorithm used to calculate a decomposition matrix related to the selected spectrum. In other instances, the decomposition model is a linear regression or spectral clustering model implemented in an artificial neural network such as a convolutional neural network (CNN). In certain instances, the linear regression or spectral clustering model is learned based on the Cholesky algorithm, the Cholesky-Banachiewicz algorithm, the Cholesky-Crout algorithm, or any combination thereof. Although aspects of the present disclosure are discussed with respect to linear algebraic decomposition techniques such as the Cholesky algorithm, the Cholesky-Banachiewicz, and the Cholesky-Crout algorithm, it should be understood that non-linear algebraic decomposition techniques may be implemented as well such as Blinder-Oaxaca decomposition, or simply the Oaxaca decomposition.

In some instances, determining whether the selected spectrum is reproducible based on spectrum within the basis set of spectra is an all or nothing determination. For example, the linear combination of spectrum from the basis set of spectra must be capable of identically reproducing (e.g., all peaks, intensities, and wavelengths match-up) the selected spectrum. In other instances, determining whether the selected spectrum is reproducible based on spectrum within the basis set of spectra is a flexible determination made in accordance with an error term or a predetermined threshold. For example, the linear combination of spectrum from the basis set of spectra may only have to be capable of reproducing 95-100% (e.g., a subset of peaks, intensities, and/or wavelengths match-up) the selected spectrum. The error term or predetermined threshold may be anything greater than or equal to a 95% match or reproducibility, e.g., 95%, 96%, 97%, 98%, or 99%.

At step 125, as illustrated in FIG. 3, when the decomposition algorithm or model is able to be decompose the selected spectrum (e.g., spectrum 310)(i.e., reproduce the selected spectrum using spectrum within the basis set of spectra), the selected spectrum is not added to the basis set of spectra. In other words, the decision is made that the selected spectrum represents a composite sample and because the basis set of spectra is intended to only comprise pure compounds the selected spectrum is not added to the basis set of spectra. In step 130, as illustrated in FIG. 3, when the decomposition algorithm or model is unable to be decompose the selected spectrum (e.g., spectrum 305)(i.e., unable to reproduce the selected spectrum using spectrum within the basis set of spectra), the selected spectrum is added to the basis set of spectra. In other words, the decision is made that the selected spectrum represents a pure sample and because the basis set of spectra is intended to only comprise pure compounds the selected spectrum is added to the basis set of spectra.

Occasionally a composite sample will be inadvertently added into the basis set of spectra (e.g., when the basis set of spectra does not include spectrum for decomposing). In order to identify and remove these inadvertent additions to the basis set of spectra, the exclusion search of the basis set 104 will be initiated and performed each time at step 130 that a selected spectrum is added to the basis set of spectra. The exclusion search of the basis set of spectra 104 includes various steps that are performed iteratively to search the entire basis set of spectra (i.e., cycle through all spectrum within the basis set of spectra) and exclude or remove spectrum representative of composite samples. As part of the exclusion search of the basis set of spectra, at step 135, a spectrum from the basis set of spectra is selected to serve as an input to a decomposition algorithm or model. The decomposition algorithm or model, as described in detail with reference to FIG. 3, may form a part of the techniques described herein to search, decompose input spectra into their respective chemical components, and exclude those spectrum representing composite samples that can be decomposed. The spectrum may be selected from the basis set of spectra by various approaches. For example, the basis set of spectra may be pre-processed to sort the spectra based on the number of peaks as described with respect to step 110 and FIG. 2, and the spectrum may be selected from the sorted spectra (e.g., the spectrum may be selected from the basis set of spectra starting at spectrum with a greatest amount of peaks and proceeding through the basis set of spectra to spectrum with a least amount of peaks). Whichever approach is used to select the spectrum, it is imperative to be able to track or maintain a record of the spectrum that have already been selected and processed by the exclusion search of the basis set of spectra 104 such that all spectrum within the basis set of spectra are selected and processed without inefficient replication of processing.

At step 140, the decomposition algorithm or model attempts to reproduce the selected spectrum based on spectrum remaining within the basis set of spectra. The decomposition algorithm or model is implemented as discussed with respect to step 120. Accordingly, the decomposition algorithm or model works to differentiate spectrum representative of a pure sample, which are intended to be left within the basis set of spectra, from spectrum representative of composite samples, which are intended to be removed from the basis set of spectra. At step 145, when the decomposition algorithm or model is able to be decompose the selected spectrum (i.e., reproduce the selected spectrum using spectrum within the basis set of spectra), the selected spectrum is removed from the basis set of spectra. In other words, the decision is made that the selected spectrum represents a composite sample and because the basis set of spectra is intended to only comprise pure compounds the selected spectrum is removed from the basis set of spectra. In step 150, when the decomposition algorithm or model is unable to be decompose the selected spectrum (i.e., unable to reproduce the selected spectrum using spectrum within the basis set of spectra), the selected spectrum is added back into the basis set of spectra. In other words, the decision is made that the selected spectrum represents a pure sample and because the basis set of spectra is intended to only comprise pure compounds the selected spectrum is added back into the basis set of spectra. The exclusion search of the basis set of spectra 104 is performed iteratively (repeating steps 135-150) to cycle through all spectrum within the basis set of spectra and exclude or remove spectrum representative of composite samples.

At step 155, the process iteratively returns to step 115 (repeating steps 115-150) to cycle through all spectrum within the initial set of spectra and add spectrum representative of pure samples to the basis set of spectra. Once all of the spectrum within the initial set of spectra have been processed, the built basis set of spectra may be provided. For example, the basis set of spectra may be stored in a storage device, communicated to a separate computing device, displayed on a user device, or the like. In some embodiments, an action is taken using the basis set of spectra. For example, the basis set of spectra may be used in the prediction of a composition of a material 106. The prediction of a composition of a material 106 includes various steps that are performed to deduce the composition of a material from a spectrogram. As part of the prediction of a composition of a material 106, at step 160, the basis set of spectra may be used to build or train one or more models to be deployed and used in downstream processing. The one or more models can be a machine-learning model implemented in an deep learning networks, such as a convolutional neural network ("CNN"), e.g. an inception neural network, a residual neural network ("Resnet"), a U-Net, a V-Net, a single shot multibox detector ("SSD") network, or a recurrent neural network ("RNN"), e.g., long short-term memory ("LSTM") models or gated recurrent units ("GRUs") models, or any combination thereof. The model can also be any other suitable ML model trained in classification of material from a spectrogram, such as a three-dimensional CNN ("3DCNN"), a dynamic time warping ("DTW") technique, a hidden Markov model ("HMM"), etc., or combinations of one or more of such techniques—e.g., CNN-HMM or MCNN (Multi-Scale Convolutional Neural Network).

The training process for the one or more models may include selecting hyperparameters for the one or more models and performing iterative operations of inputting spectrum from the basis set of spectra into the one or more model to find a set of model parameters (e.g., weights and/or biases) that minimizes a loss or error function for the one or more models. The hyperparameters are settings that can be tuned or optimized to control the behavior of the one or more models. Most models explicitly define hyperparameters that control different aspects of the models such as memory or cost of execution. However, additional hyperparameters may be defined to adapt a model to a specific scenario. For example, the hyperparameters may include the number of hidden units of a model, the learning rate of a model, the convolution kernel width, or the number of kernels for a model. Each iteration of training can involve finding a set of model parameters for the one or more models (configured with a defined set of hyperparameters) so that the value of the loss or error function using the set of model parameters is smaller than the value of the loss or error function using a different set of model parameters in a previous iteration. The loss or error function can be constructed to measure the difference between the outputs inferred using the models (in some instances, the classification of components of a material represented by a spectrum) and the ground truth spectra from the basis set of spectra.

The model training step 160 outputs one or more trained models. At step 165, the one or more trained models may be deployed within a material processing operation for which a wide array of materials serve as potential feedstocks for a material recycling and/or up-cycling process. At step 170, the one or more trained models may be used to deduce the composition of the material from a spectrogram of the material for accurate material characterization, sorting, and/or decomposition yield prediction. Advantageously, the basis set of spectra is constructed as library or database of spectra with fine grained labeling due to the characteristic nature of the spectra representing only "pure" samples. For example, all or substantially all additives and misleading information associated with the additives has been removed from the spectra (as compared to conventional libraries or databases of spectra such as the initial set of spectra) such that characteristics of the spectra are directly relatable to the "pure" samples and can be used to more accurately train models to deduce the composition of a material.

FIG. 4 illustrates a flowchart for an exemplary process 400 for deducing the composition of the material from a spectrogram using a neural network model trained on a basis set of spectra representing pure samples obtained in accordance with aspects of the present disclosure. Process 400 may be performed using one or more computing systems, models, and networks, as described with respect to FIGS. 1-3 and 5. Process 400 begins at block 405 where an initial set of spectra is obtained for a plurality of samples comprising pure samples and composite samples. At block 410, the initial set of spectra are sorted based on a characteristic observed within each spectrum such as a number of peaks observed within each spectrum At block 415, a basis set of spectra for a plurality of pure samples is constructed based on the initial set of spectra. The constructing the basis set of spectra comprises: (i) selecting a spectrum from the initial set of spectra. In some instances, the spectrum are selected from the initial set of spectra based on the sorting performed in block 410. For example, selecting a spectrum from the initial set of spectra starting at spectrum with a least amount of peaks and proceeding through the initial set of spectra to spectrum with a greatest amount of peaks. The constructing the basis set of spectra further comprises: (ii) attempting to decompose, using a decomposition algorithm or model, the selected spectrum based on spectrum within the basis set of spectra. In some instances, the decomposition algorithm or model is a decomposition algorithm and the decomposition algorithm is the Cholesky algorithm, the Cholesky-Banachiewicz algorithm, the Cholesky-Crout algorithm, or any combination thereof. In other instances, the decomposition algorithm or model is a decomposition model and the decomposition model is implemented in an artificial neural network. The decomposition model may be a linear regression or spectral clustering model and the linear regression or spectral clustering model may be learned based on the Cholesky algorithm, the Cholesky-Banachiewicz algorithm, the Cholesky-Crout algorithm, or any combination thereof. In certain instances, the attempting to decompose the selected spectrum or the removed spectrum comprises determining whether the selected spectrum or the removed spectrum is reproducible based on the spectrum within the basis set of spectra, and the determining whether the selected spectrum or the removed spectrum is reproducible is a flexible determination made in accordance with a predetermined threshold set at greater than or equal to 65% reproducibility.

The constructing the basis set of spectra further comprises: (iii) when the selected spectrum is unable to be decomposed, adding the selected spectrum to the basis set of spectra; and (iv) in response to adding the selected spectrum to the basis set of spectra, performing an exclusion search of the basis set of spectra that includes: (a) removing each spectrum from the basis set of spectra, (b) attempting to decompose, using the decomposition algorithm or model, each removed spectrum based on spectrum remaining within the basis set of spectra, and (c) when a removed spectrum is able to be decomposed, identifying the removed spectrum as a composite sample and leaving the removed spectrum out of the basis set of spectra, or (d) when the removed spectrum is unable to be decomposed, identifying the removed spectrum as a pure sample and adding the spectrum back into the basis set of spectra. Steps (a)-(d) are performed iteratively until all spectrum from the basis set of spectra are processed. Steps (i)-(v) are performed iteratively until all spectrum from the initial set of spectra are processed.

At block 420, the basis set of spectra is provided. For example, the basis set of spectra may be stored in a storage device, communicated to a separate computing device, displayed on a user device, or the like. At block 425, a spectrogram is obtained for a material. In some instances, the spectrogram is obtained in a recycling or upcycling operation employed in a recycling and/or manufacturing plant. The material may include metals, glass, bio-polymers such as ligno-cellulosic materials, visco-elastic materials, minerals such as rare earth containing materials, as well as complex composite materials or devices. At block 430, the spectrogram is input into a neural network model trained for classification of chemical components using a loss function and the basis set of spectra. More specifically, the neural network model comprises a plurality of model parameters identified using a set of training data comprising the basis set of spectra maps, and the plurality of model parameters are identified using the set of training data based on minimizing the loss function. At block 435, one or more chemical components of the material are identified and classified using the neural network model. At block 440, the classification for each of the one or more chemical components is output. For example, the classification for each of the one or more chemical components may be stored in a storage device, communicated to a separate computing device, displayed on a user device, or the like. Thereafter, the classification for each of the one or more chemical components may be used to characterize the material, sort the material from other materials, predict decomposition yield of the material, or any combination thereof. The characterization, sorting, and/or prediction of yield of the material may be used in downstream processes for recycling the material or feedstock comprising the material by chemical and/or physical decomposition into the one or more chemical components and/or manufacturing a target product using the one or more chemical components of the material.

III. SYSTEM ENVIRONMENT

Figure 5:
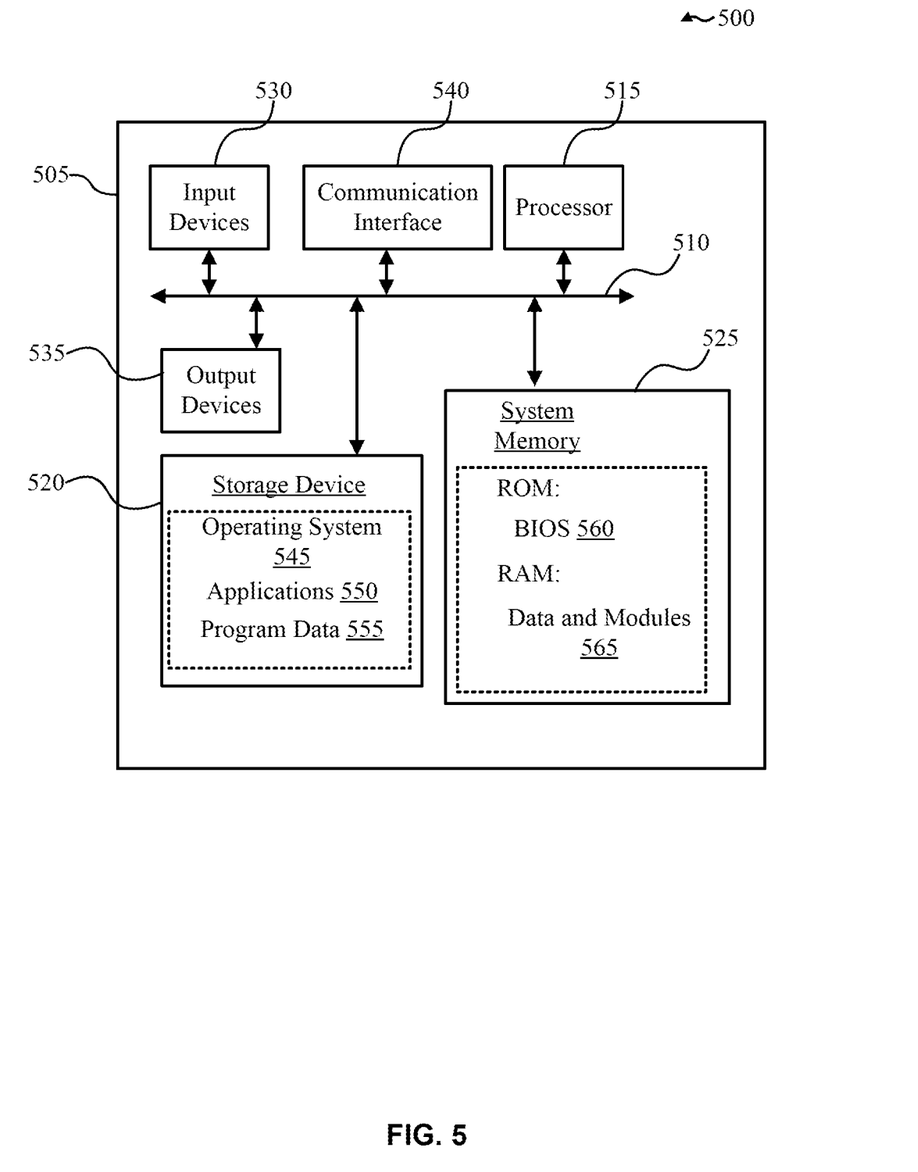
FIG. 5 illustrates an architecture of a computing system implemented in accordance with some embodiments of the present disclosure.

FIG. 5 is an illustrative architecture of a computing system 500 implemented as some embodiments of the present disclosure. The computing system 500 is only one example of a suitable computing system and is not intended to suggest any limitation as to the scope of use or functionality of the present disclosure. Also, computing system 500 should not be interpreted as having any dependency or requirement relating to any one or combination of components illustrated in computing system 500.

As shown in FIG. 5, computing system 500 includes a computing device 505. The computing device 505 can be resident on a network infrastructure such as within a cloud environment, or may be a separate independent computing device (e.g., a computing device of a service provider). The computing device 505 may include a bus 510, processor 515, a storage device 520, a system memory (hardware device) 525, one or more input devices 530, one or more output devices 535, and a communication interface 540.

The bus 510 permits communication among the components of computing device 505. For example, bus 510 may be any of several types of bus structures including a memory bus or memory controller, a peripheral bus, and a local bus using any of a variety of bus architectures to provide one or more wired or wireless communication links or paths for transferring data and/or power to, from, or between various other components of computing device 505.

The processor 515 may be one or more processors, microprocessors, or specialized dedicated processors that include processing circuitry operative to interpret and execute computer readable program instructions, such as program instructions for controlling the operation and performance of one or more of the various other components of computing device 505 for implementing the functionality, steps, and/or performance of various embodiments described herein. In certain embodiments, processor 515 interprets and executes the processes, steps, functions, and/or operations of the various embodiments, which may be operatively implemented by the computer readable program instructions. For example, processor 515 can retrieve, e.g., import and/or otherwise obtain or construct spectra, implement a decomposition algorithm or model, provide or output spectra, implement one or more machine learning models, output components of a material analyzed in accordance with spectra, assist in decomposition of a material into components, assist in the manufacture of a target product using the components of the material, or the like. In embodiments, the information obtained or generated by the processor 515, e.g., the initial set of spectra, the basis set of spectra, the components of the material, classification of the components, etc., can be stored in the storage device 520.

The storage device 520 may include removable/non-removable, volatile/non-volatile computer readable media, such as, but not limited to, non-transitory machine readable storage medium such as magnetic and/or optical recording media and their corresponding drives. The drives and their associated computer readable media provide for storage of computer readable program instructions, data structures, program modules and other data for operation of computing device 505 in accordance with the different aspects of the present disclosure. In embodiments, storage device 520 may store operating system 545, application programs 550, and program data 555 in accordance with aspects of the present disclosure.

The system memory 525 may include one or more storage mediums, including for example, non-transitory machine readable storage medium such as flash memory, permanent memory such as read-only memory ("ROM"), semi-permanent memory such as random access memory ("RAM"), any other suitable type of non-transitory storage component, or any combination thereof. In some embodiments, an input/output system 560 (BIOS) including the basic routines that help to transfer information between the various other components of computing device 505, such as during start-up, may be stored in the ROM. Additionally, data and/or program modules 565, such as at least a portion of operating system 545, program modules, application programs 550, and/or program data 555, that are accessible to and/or presently being operated on by processor 515, may be contained in the RAM. In embodiments, the program modules 565 and/or application programs 550 can comprise, for example, a deformulation tool, a decomposition algorithm or model, and a neural network model to deformulate/decompose spectra, build a basis set of spectra, identify components of a material analyzed in accordance with spectra, assist in decomposition of a material into components, assist in the manufacture of a target product using the components of the material, or the like which provides the instructions for execution of processor 515.

The one or more input devices 530 may include one or more mechanisms that permit an operator to input information to computing device 505, such as, but not limited to, a touch pad, dial, click wheel, scroll wheel, touch screen, one or more buttons (e.g., a keyboard), mouse, game controller, track ball, microphone, camera, proximity sensor, light detector, motion sensors, biometric sensor, and combinations thereof. The one or more output devices 535 may include one or more mechanisms that output information to an operator, such as, but not limited to, audio speakers, headphones, audio line-outs, visual displays, antennas, infrared ports, tactile feedback, printers, or combinations thereof.

The communication interface 540 may include any transceiver-like mechanism (e.g., a network interface, a network adapter, a modem, or combinations thereof) that enables computing device 505 to communicate with remote devices or systems, such as a mobile device or other computing devices such as, for example, a server in a networked environment, e.g., cloud environment. For example, computing device 505 may be connected to remote devices or systems via one or more local area networks (LAN) and/or one or more wide area networks (WAN) using communication interface 640.

As discussed herein, computing system 500 may be configured to decompose input spectra into their respective chemical components and build a basis set of spectra representing pure samples that can be used to ultimately deduce the composition of a material from a spectrogram. In particular, computing device 505 may perform tasks (e.g., process, steps, methods and/or functionality) in response to processor 515 executing program instructions contained in non-transitory machine readable storage medium, such as system memory 525. The program instructions may be read into system memory 525 from another computer readable medium (e.g., non-transitory machine readable storage medium), such as data storage device 520, or from another device via the communication interface 540 or server within or outside of a computing environment. In embodiments, an operator may interact with computing device 505 via the one or more input devices 530 and/or the one or more output devices 535 to facilitate performance of the tasks and/or realize the end results of such tasks in accordance with aspects of the present disclosure. In additional or alternative embodiments, hardwired circuitry may be used in place of or in combination with the program instructions to implement the tasks, e.g., steps, methods and/or functionality, consistent with the different aspects of the present disclosure. Thus, the steps, methods and/or functionality disclosed herein can be implemented in any combination of hardware circuitry and software.

IV. EXAMPLES

The systems and methods implemented in various embodiments may be better understood by referring to the following examples.

Spectra collected from composite materials are generally convoluted and, as such, may include characteristic features of multiple constituent materials. Decomposition of a sample spectra may include spectral deconvolution by linear combination, which describes a technique whereby several characteristic spectra of pure materials are combined to generate a sum spectrum. Individual characteristic spectra are normalized to a maximum intensity in each respective spectrum, and are then weighted by an adjustable weighting factor before being linearly combined. The weighting factors for each constituent spectrum may be adjusted such that for the sum spectrum the sum of the weighting factors is one. The weighting factors may be generated by estimating an error function, such as a sum of squares error function or a least squares error function, describing the accuracy of the sum spectrum to correspond to a sample spectrum. Minimizing the error function may permit the weighting factors to be generated. The techniques described above in reference to Cholesky algorithm variants may serve as additional approaches to spectral decomposition.

In an illustrative example, Tween 65 is a is a fatty acid polyoxyethylene ester of sorbitan that is highly effective at forming oil-in-water emulsions. Tween 65 is applied in bitumen extraction and upgrading, chemicals manufacturing, emulsification, and in nonwoven plastics manufacturing. As such, Tween 65 is sometimes detected in waste materials and may be an additive or a contaminant in waste material feedstocks. Chemically, Tween 65 is itself a composite material including several constituent materials, each having a characteristic spectrum measurable by spectroscopy. In this way, when Tween 65 is characterized by vibrational spectroscopy, the spectrum produced is a sum spectrum including contributions from each constituent material. Furthermore, based on approximations arising from an assumption that the constituent materials are non-reactive and do not exhibit interaction with respect to absorbance in infrared wavelengths, each constituent material contributes to the sum spectrum in proportion to the composition of the composite material (e.g., by the Beer-Lambert Approximation).

The exact composition of Tween 65 is proprietary and, as such, the sum spectrum may be generated by predicting the component spectra from a basis set of characteristic spectra of pure materials. Including an entire basis set may increase computational resource demand of the spectral decomposition process, so the basis set may be filtered to remove materials that are incompatible with emulsifier applications or that do not fit the properties of Tween 65. The characteristic spectra, normalized to a peak intensity of one, may be weighted by a variable weighting factor and summed together, after which the error may be calculated between the sum spectrum and the sample spectrum. After several iterations, where the weighting factors may be modified and the error re-estimated, a large portion of the characteristic basis set may be removed from further calculations in cases where the weighting factor drops below a threshold value or converges toward zero. In this way, the number and relative composition of constituent materials in Tween 65 may be predicted by decomposing the sample spectrum into thirteen or more constituent materials, each making up at least 1% of the overall material composition. For Tween 65, an example spectral decomposition may include the following thirteen components, with the weighting factor in parentheses: (0.21) Poloxamer 105, (0.20) PEG 400 Monooleate, (0.13) Polyglyceryl Oleate, (0.12) Poly(ethylene glycol), (0.10) Hydropalat, (0.04) Brij 35 Polyoxyethylene 35 Lauryl Ether, (0.03) Poly(ethylene glycol), (0.03), Polychlortrifluorethylen Fluorolube, (0.03) Di(ethylene glycol) distearate, (0.03) Diethylene Glycol Monostearate, (0.02) Phosphate Potassium Dibasic Trihydrate. (0.02) Polyoxymethylene, and (0.01) Benzenesulfonic acid. The sum of the weighting factors for this predicted spectral decomposition is 0.97.

Figure 6:
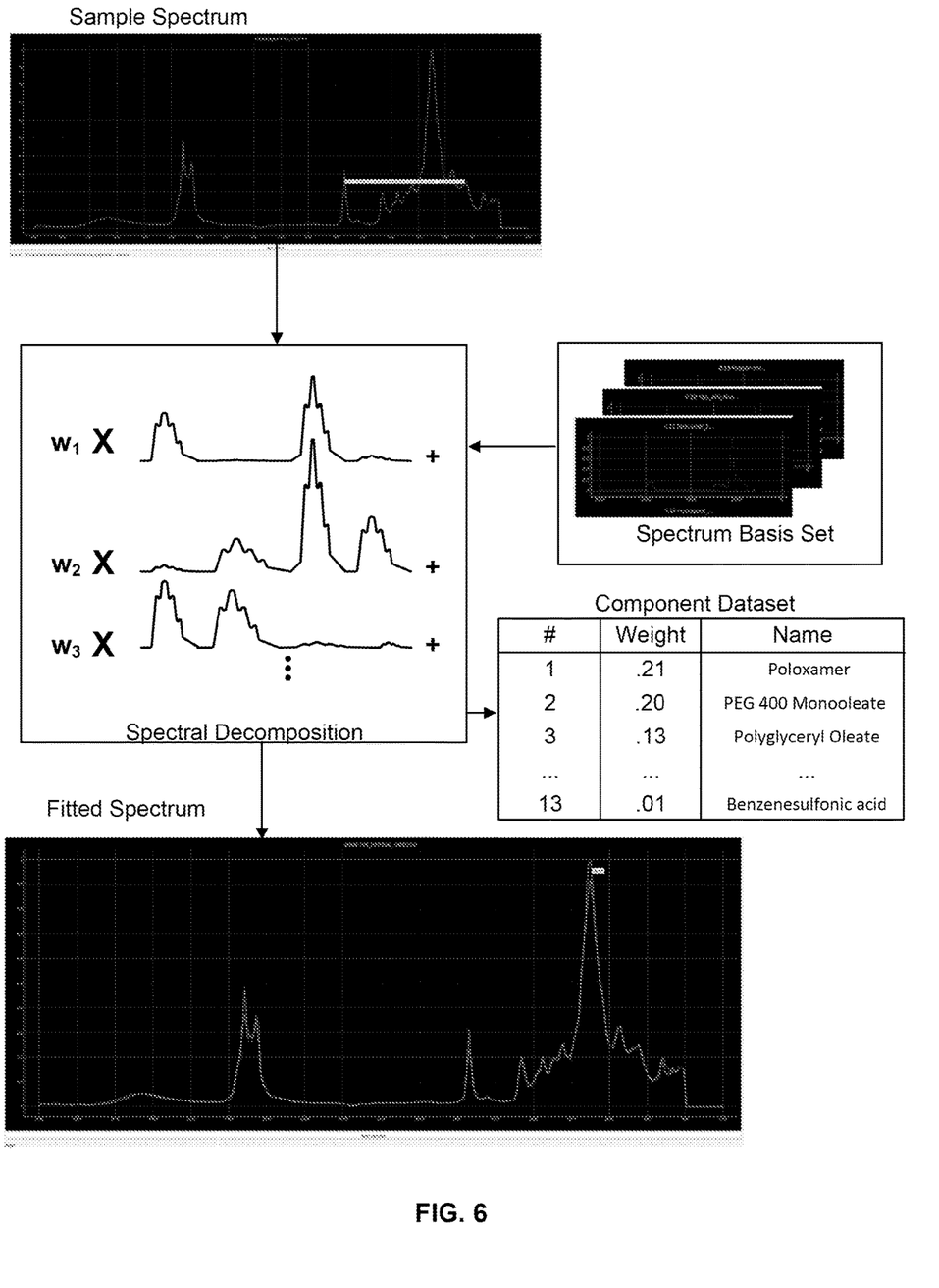
FIG. 6 illustrates an exemplary spectral decomposition in accordance with some embodiments of the present disclosure.

In reference to FIG. 6, a spectral decomposition is illustrated for the first four entries on the preceding list, making up 67% of the sum spectrum. The process illustrated in FIG. 6 is a simplification to better illustrate spectral decomposition without a visual summation of thirteen characteristic spectra, eight of which are significant to error calculation, but nonetheless are reduced by more than 95% in peak intensity prior to summation and, as such, are less visually informative. In FIG. 6, a sample spectrum for Tween 65 is input to a spectral decomposition process, for which a basis set of spectra are provided, each intensity-normalized to 1. A weight factor is applied to each spectrum from the basis set and the spectra are summed. After converging to a solution set of component spectra, using, for example, an error estimation, the spectrum decomposition outputs a sum spectrum and data describing the constituent materials making up Tween 65 with corresponding weights for the basis set spectra that are included. As described above, in the example described for Tween 65, the number of component spectra is limited to those with a weight of at least 0.1.

V. ADDITIONAL CONSIDERATIONS

Specific details are given in the above description to provide a thorough understanding of the embodiments. However, it is understood that the embodiments can be practiced without these specific details. For example, circuits can be shown in block diagrams in order not to obscure the embodiments in unnecessary detail. In other instances, well-known circuits, processes, algorithms, structures, and techniques can be shown without unnecessary detail in order to avoid obscuring the embodiments.

Implementation of the techniques, blocks, steps and means described above can be done in various ways. For example, these techniques, blocks, steps and means can be implemented in hardware, software, or a combination thereof. For a hardware implementation, the processing units can be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above, and/or a combination thereof.

Also, it is noted that the embodiments can be described as a process which is depicted as a flowchart, a flow diagram, a data flow diagram, a structure diagram, or a block diagram. Although a flowchart can describe the operations as a sequential process, many of the operations can be performed in parallel or concurrently. In addition, the order of the operations can be re-arranged. A process is terminated when its operations are completed, but could have additional steps not included in the figure. A process can correspond to a method, a function, a procedure, a subroutine, a subprogram, etc. When a process corresponds to a function, its termination corresponds to a return of the function to the calling function or the main function.

Furthermore, embodiments can be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks can be stored in a machine readable medium such as a storage medium. A code segment or machine-executable instruction can represent a procedure, a function, a subprogram, a program, a routine, a subroutine, a module, a software package, a script, a class, or any combination of instructions, data structures, and/or program statements. A code segment can be coupled to another code segment or a hardware circuit by passing and/or receiving information, data, arguments, parameters, and/or memory contents. Information, arguments, parameters, data, etc. can be passed, forwarded, or transmitted via any suitable means including memory sharing, message passing, ticket passing, network transmission, etc.

For a firmware and/or software implementation, the methodologies can be implemented with modules (e.g., procedures, functions, and so on) that perform the functions described herein. Any machine-readable medium tangibly embodying instructions can be used in implementing the methodologies described herein. For example, software codes can be stored in a memory. Memory can be implemented within the processor or external to the processor. As used herein the term "memory" refers to any type of long term, short term, volatile, nonvolatile, or other storage medium and is not to be limited to any particular type of memory or number of memories, or type of media upon which memory is stored.

Moreover, as disclosed herein, the term "storage medium", "storage" or "memory" can represent one or more memories for storing data, including read only memory (ROM), random access memory (RAM), magnetic RAM, core memory, magnetic disk storage mediums, optical storage mediums, flash memory devices and/or other machine readable mediums for storing information. The term "machine-readable medium" includes, but is not limited to portable or fixed storage devices, optical storage devices, wireless channels, and/or various other storage mediums capable of storing that contain or carry instruction(s) and/or data.

While the principles of the disclosure have been described above in connection with specific apparatuses and methods, it is to be clearly understood that this description is made only by way of example and not as limitation on the scope of the disclosure.

What is claimed is:

1. A computer-implemented method comprising:
obtaining an initial set of spectra for a plurality of samples comprising pure samples and composite samples;
constructing a basis set of spectra for a plurality of pure samples based on the initial set of spectra, wherein the constructing the basis set of spectra comprises:
(i) selecting a spectrum from the initial set of spectra;
(ii) attempting to decompose, using a decomposition algorithm or model, the selected spectrum based on spectrum within the basis set of spectra,
(iii) when the selected spectrum is unable to be decomposed, adding the selected spectrum to the basis set of spectra; and
(iv) in response to adding the selected spectrum to the basis set of spectra, performing an exclusion search of the basis set of spectra that includes iteratively removing each spectrum from the basis set of spectra, attempting to decompose, using the decomposition algorithm or model, each removed spectrum based on spectrum remaining within the basis set of spectra, and when a removed spectrum is unable to be decomposed, identifying the removed spectrum as a pure sample and adding the spectrum back into the basis set of spectra,
wherein steps (i)-(v) are performed iteratively until all spectrum from the initial set of spectra are processed; and
providing the basis set of spectra.

2. The computer-implemented method of claim 1, further comprising prior to constructing the basis set, sorting the initial set of spectra based on a number of peaks observed within each spectrum, wherein the spectrum are selected from the initial set of spectra starting at spectrum with a least amount of peaks and proceeding through the initial set of spectra to spectrum with a greatest amount of peaks.

3. The computer-implemented method of claim 1, wherein the decomposition algorithm or model is a decomposition algorithm and the decomposition algorithm is the Cholesky algorithm, the Cholesky-Banachiewicz algorithm, the Cholesky-Crout algorithm, or any combination thereof.

4. The computer-implemented method of claim 1, wherein the decomposition algorithm or model is a decomposition model and the decomposition model is implemented in an artificial neural network.

5. The computer-implemented method of claim 4, wherein the decomposition model is a linear regression or spectral clustering model and the linear regression or spectral clustering model is learned based on the Cholesky algorithm, the Cholesky-Banachiewicz algorithm, the Cholesky-Crout algorithm, or any combination thereof.

6. The computer-implemented method of claim 1, wherein the attempting to decompose the selected spectrum or the removed spectrum comprises determining whether the selected spectrum or the removed spectrum is reproducible based on the spectrum within the basis set of spectra, and wherein the determining whether the selected spectrum or the removed spectrum is reproducible is a flexible determination made in accordance with a predetermined threshold set at greater than or equal to 65% reproducibility.

7. The computer-implemented method of claim 1, further comprising:
obtaining a spectrogram for a material;
inputting the spectrogram into a neural network model trained for classification of chemical components using a loss function and the basis set of spectra;
identifying and classifying, using the neural network model, one or more chemical components within the spectrogram; and
outputting, using the neural network, the classification for each of the one or more chemical components.

8. The computer-implements method of claim 7, wherein the neural network model comprises a plurality of model parameters identified using a set of training data comprising the basis set of spectra maps, and wherein the plurality of model parameters are identified using the set of training data based on minimizing the loss function.

9. The computer-implemented method of claim 7, further comprising using the classification for each of the one or more chemical components to characterize the material, sort the material from other materials, predict decomposition yield of the material, or any combination thereof.

10. The computer-implemented method of claim 9, further comprising chemically and/or physically decomposing the material into the one or more chemical components, and manufacturing a target product using the one or more chemical components based on the characterization, sorting and/or yield prediction of the material.

11. A computer-program product tangibly embodied in a non-transitory machine-readable storage medium, including instructions configured to cause one or more data processors to perform actions including:
obtaining an initial set of spectra for a plurality of samples comprising pure samples and composite samples;
constructing a basis set of spectra for a plurality of pure samples based on the initial set of spectra, wherein the constructing the basis set of spectra comprises:
(i) selecting a spectrum from the initial set of spectra;
(ii) attempting to decompose, using a decomposition algorithm or model, the selected spectrum based on spectrum within the basis set of spectra,
(iii) when the selected spectrum is unable to be decomposed, adding the selected spectrum to the basis set of spectra; and
(iv) in response to adding the selected spectrum to the basis set of spectra, performing an exclusion search of the basis set of spectra that includes iteratively removing each spectrum from the basis set of spectra, attempting to decompose, using the decomposition algorithm or model, each removed spectrum based on spectrum remaining within the basis set of spectra, and when a removed spectrum is unable to be decomposed, identifying the removed spectrum as a pure sample and adding the spectrum back into the basis set of spectra,
wherein steps (i)-(v) are performed iteratively until all spectrum from the initial set of spectra are processed; and
providing the basis set of spectra.

12. The computer-program product of claim 11, wherein the actions further include prior to constructing the basis set, sorting the initial set of spectra based on a number of peaks observed within each spectrum, wherein the spectrum are selected from the initial set of spectra starting at spectrum with a least amount of peaks and proceeding through the initial set of spectra to spectrum with a greatest amount of peaks.

13. The computer-program product of claim 11, wherein the attempting to decompose the selected spectrum or the removed spectrum comprises determining whether the selected spectrum or the removed spectrum is reproducible based on the spectrum within the basis set of spectra, and wherein the determining whether the selected spectrum or the removed spectrum is reproducible is a flexible determination made in accordance with a predetermined threshold set at greater than or equal to 65% reproducibility.

14. The computer-program product of claim 11, wherein the actions further include:
   obtaining a spectrogram for a material;
      inputting the spectrogram into a neural network model trained for classification of chemical components using a loss function and the basis set of spectra;
      identifying and classifying, using the neural network model, one or more chemical components within the spectrogram; and
   outputting, using the neural network, the classification for each of the one or more chemical components,
   wherein the neural network model comprises a plurality of model parameters identified using a set of training data comprising the basis set of spectra maps, and wherein the plurality of model parameters are identified using the set of training data based on minimizing the loss function.

15. The computer-program product of claim 14, wherein the actions further include using the classification for each of the one or more chemical components to characterize the material, sort the material from other materials, predict decomposition yield of the material, or any combination thereof.

16. A system comprising:
   one or more data processors; and
   a non-transitory computer readable storage medium containing instructions which, when executed on the one or more data processors, cause the one or more data processors to perform actions including:
   obtaining an initial set of spectra for a plurality of samples comprising pure samples and composite samples;
   constructing a basis set of spectra for a plurality of pure samples based on the initial set of spectra, wherein the constructing the basis set of spectra comprises:
      (i) selecting a spectrum from the initial set of spectra;
      (ii) attempting to decompose, using a decomposition algorithm or model, the selected spectrum based on spectrum within the basis set of spectra,
      (iii) when the selected spectrum is unable to be decomposed, adding the selected spectrum to the basis set of spectra; and
      (iv) in response to adding the selected spectrum to the basis set of spectra, performing an exclusion search of the basis set of spectra that includes iteratively removing each spectrum from the basis set of spectra, attempting to decompose, using the decomposition algorithm or model, each removed spectrum based on spectrum remaining within the basis set of spectra, and when a removed spectrum is unable to be decomposed, identifying the removed spectrum as a pure sample and adding the spectrum back into the basis set of spectra,
   wherein steps (i)-(v) are performed iteratively until all spectrum from the initial set of spectra are processed; and
   providing the basis set of spectra.

17. The system of claim 16, wherein the actions further include prior to constructing the basis set, sorting the initial set of spectra based on a number of peaks observed within each spectrum, wherein the spectrum are selected from the initial set of spectra starting at spectrum with a least amount of peaks and proceeding through the initial set of spectra to spectrum with a greatest amount of peaks.

18. The system of claim 16, wherein the attempting to decompose the selected spectrum or the removed spectrum comprises determining whether the selected spectrum or the removed spectrum is reproducible based on the spectrum within the basis set of spectra, and wherein the determining whether the selected spectrum or the removed spectrum is reproducible is a flexible determination made in accordance with a predetermined threshold set at greater than or equal to 65% reproducibility.

19. The system of claim 16, wherein the actions further include:
   obtaining a spectrogram for a material;
      inputting the spectrogram into a neural network model trained for classification of chemical components using a loss function and the basis set of spectra;
      identifying and classifying, using the neural network model, one or more chemical components within the spectrogram; and
   outputting, using the neural network, the classification for each of the one or more chemical components,
   wherein the neural network model comprises a plurality of model parameters identified using a set of training data comprising the basis set of spectra maps, and wherein the plurality of model parameters are identified using the set of training data based on minimizing the loss function.

20. The system of claim 19, wherein the actions further include using the classification for each of the one or more chemical components to characterize the material, sort the material from other materials, predict decomposition yield of the material, or any combination thereof.

* * * * *